United States Patent
Wright et al.

(10) Patent No.: US 9,522,854 B2
(45) Date of Patent: Dec. 20, 2016

(54) PROCESS AND APPARATUS FOR THE SELECTIVE DIMERIZATION OF TERPENES AND POLY-ALPHA-OLEFINS WITH A SINGLE-STAGE REACTOR AND A SINGLE-STAGE FRACTIONATION SYSTEM

(75) Inventors: Michael E. Wright, Ridgecrest, CA (US); Benjamin G. Harvey, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 1310 days.

(21) Appl. No.: 13/426,347

(22) Filed: Mar. 21, 2012

(65) Prior Publication Data

US 2012/0207648 A1 Aug. 16, 2012

Related U.S. Application Data

(60) Continuation-in-part of application No. 12/511,796, filed on Jul. 29, 2009, now Pat. No. 8,395,007, and a
(Continued)

(51) Int. Cl.
*B01J 8/04* (2006.01)
*C07C 2/08* (2006.01)
(Continued)

(52) U.S. Cl.
CPC .. *C07C 2/28* (2013.01); *B01J 8/04* (2013.01); *C07C 2/08* (2013.01); *C07C 5/03* (2013.01);
(Continued)

(58) Field of Classification Search
None
See application file for complete search history.

(56) References Cited

U.S. PATENT DOCUMENTS 2,249,112 A * 7/1941 Carmody ............... C07C 5/03
525/339
4,165,301 A * 8/1979 Wiegers ............... C11B 9/00
510/104
(Continued)

FOREIGN PATENT DOCUMENTS

EP 0173471 B1 6/1989
WO WO 2010/055935 A1 5/2010
(Continued)

OTHER PUBLICATIONS

Williams, et al., "Kineticstudies of catalyticdehydration of tert-butanol on zeolite NaH—ZSM-5"; Journal of Catalysis [online], Jan. 1991, vol. 127, Iss. 1, pp. 377-392.
(Continued)

*Primary Examiner* — Jennifer A Leung
(74) *Attorney, Agent, or Firm* — Charlene A Haley

(57) ABSTRACT

An improved process and apparatus for the selective reaction of terpenes (including mono-, sesqui-, di-terpenes, and others in the terpene family), alpha-olefin oligomers (OOA's), and related olefins to their respective dimeric product in high purity using heterogeneous acid catalyst concurrent with full utilization of energy created in the process. Embodiments of the invention carry out a unique and highly efficient dimerization of terpenes, alpha-olefin oligomers (OOA's), and olefins using cost effective catalysts and low cost equipment that are ideally suited for commercialization of jet/turbine and diesel biofuel processes producing fuels with high flashpoints and superb cold flow properties.

18 Claims, 3 Drawing Sheets

Related U.S. Application Data continuation-in-part of application No. 12/550,973, filed on Aug. 31, 2009, now Pat. No. 8,227,651, and a division of application No. 13/426,294, filed on Mar. 21, 2012.

(51) Int. Cl.
  *C07C 2/28*  (2006.01)
  *C07C 5/03*  (2006.01)

(52) U.S. Cl.
  CPC .... *B01J 2219/0004* (2013.01); *C07C 2531/08* (2013.01)

(56) References Cited

U.S. PATENT DOCUMENTS

| | | | |
|---|---|---|---|
| 4,207,424 A | 6/1980 | Winnick | |
| 4,234,752 A | 11/1980 | Wu et al. | |
| 4,260,845 A | 4/1981 | Shioyama | |
| 4,367,352 A * | 1/1983 | Watts, Jr. | C07C 2/28 585/254 |
| 4,473,444 A | 9/1984 | Feldman et al. | |
| 4,570,026 A | 2/1986 | Keyworth et al. | |
| 4,772,736 A | 9/1988 | Edwards et al. | |
| 5,057,636 A | 10/1991 | Sweeney | |
| 5,158,992 A | 10/1992 | Caselli et al. | |
| 5,633,420 A * | 5/1997 | Theriot | C07C 2/20 585/500 |
| 5,817,899 A * | 10/1998 | Hope | C07C 9/22 585/16 |
| 5,830,821 A | 11/1998 | Rohrmann et al. | |
| 6,147,271 A | 11/2000 | Strebel et al. | |
| 6,156,689 A | 12/2000 | Kimble et al. | |
| 6,214,953 B1 | 4/2001 | Oh et al. | |
| 6,225,359 B1 | 5/2001 | O'Rear et al. | |
| 6,660,894 B1 * | 12/2003 | Wu | C10G 65/043 585/324 |
| 6,929,705 B2 | 8/2005 | Myers et al. | |
| 8,242,319 B1 | 8/2012 | Wright et al. | |
| 8,344,196 B2 | 1/2013 | Wright et al. | |
| 8,350,107 B2 | 1/2013 | Wright et al. | |
| 8,395,007 B2 | 3/2013 | Wright et al. | |
| 2001/0006154 A1 | 7/2001 | Krug et al. | |
| 2002/0091068 A1 | 7/2002 | Loper | |
| 2002/0177728 A1 | 11/2002 | Boudreaux et al. | |
| 2003/0125595 A1 | 7/2003 | Bagheri et al. | |
| 2005/0267271 A1 | 12/2005 | Mink et al. | |
| 2006/0199988 A1 * | 9/2006 | Kowalik | C10G 50/00 585/533 |
| 2007/0049781 A1 * | 3/2007 | Brown | C10G 50/00 585/517 |
| 2007/0185362 A1 | 8/2007 | Lattner et al. | |
| 2007/0293640 A1 | 12/2007 | Jiang et al. | |
| 2007/0293712 A1 | 12/2007 | Titta et al. | |
| 2008/0102502 A1 | 5/2008 | Foody et al. | |
| 2008/0132730 A1 | 6/2008 | Manzer et al. | |
| 2008/0216391 A1 | 9/2008 | Cortright et al. | |
| 2009/0124835 A1 | 5/2009 | Yamaguchi et al. | |
| 2009/0139134 A1 | 6/2009 | Yoshikuni et al. | |
| 2009/0299109 A1 | 12/2009 | Gruber et al. | |
| 2009/0305926 A1 | 12/2009 | Wu et al. | |
| 2010/0069589 A1 | 3/2010 | Bradin | |
| 2010/0155333 A1 | 6/2010 | Husain et al. | |
| 2010/0204925 A1 | 8/2010 | Albahri | |
| 2010/0317904 A1 * | 12/2010 | Small | C08F 10/14 585/18 |
| 2010/0330633 A1 | 12/2010 | Walther et al. | |
| 2011/0061290 A1 | 3/2011 | Aulich et al. | |
| 2011/0111475 A1 | 5/2011 | Kuhry et al. | |
| 2011/0114538 A1 | 5/2011 | Cosyns et al. | |
| 2011/0160502 A1 | 6/2011 | Wu et al. | |
| 2011/0172475 A1 | 7/2011 | Peters et al. | |
| 2012/0207648 A1 | 8/2012 | Wright et al. | |
| 2012/0209036 A1 | 8/2012 | Harvey et al. | |
| 2012/0209039 A1 | 8/2012 | Wright et al. | |
| 2012/0209040 A1 | 8/2012 | Wright et al. | |
| 2012/0209047 A1 | 8/2012 | Wright et al. | |
| 2012/0238788 A1 | 9/2012 | Wright et al. | |
| 2012/0271089 A1 | 10/2012 | Wright et al. | |
| 2013/0197279 A1 | 8/2013 | Wright et al. | |
| 2013/0253236 A1 | 9/2013 | Wright et al. | |

FOREIGN PATENT DOCUMENTS

| | | |
|---|---|---|
| WO | WO 2010/136289 A2 | 12/2010 |
| WO | PCT/US12/35121 | 4/2012 |
| WO | PCT/US12/35126 | 4/2012 |
| WO | PCT/US12/35132 | 4/2012 |
| WO | PCT/US12/35146 | 4/2012 |
| WO | PCT/US12/35167 | 4/2012 |
| WO | PCT/US12/41200 | 6/2012 |
| WO | PCT/US2012/035121 | 11/2012 |
| WO | PCT/US2012/035126 | 3/2013 |
| WO | WO 2013032550 | 3/2013 |
| WO | PCT/US2012/035132 | 5/2013 |
| WO | PCT/US2012/041200 | 5/2013 |
| WO | PCT/US2012/035167 | 7/2013 |
| WO | PCT/US2012/035146 | 9/2013 |
| WO | PCT/US2012/035155 | 10/2013 |
| WO | PCT/US2012/035184 | 10/2013 |
| WO | PCT/US2012/035190 | 10/2013 |
| WO | PCT/US2012/035167 | 7/2014 |

OTHER PUBLICATIONS

Leeuwen, et al., "New processes for the selective production of 1-octene"; Coordination Chemistry Reviews [online], Epub, Oct. 16, 2010, vol. 255, Iss. 13-14; pp. 1499-1517.

* cited by examiner

PROCESS AND APPARATUS FOR THE SELECTIVE DIMERIZATION OF TERPENES AND POLY-ALPHA-OLEFINS WITH A SINGLE-STAGE REACTOR AND A SINGLE-STAGE FRACTIONATION SYSTEM

CROSS-REFERENCE TO RELATED APPLICATIONS

This is a divisional application, claiming the benefit of, parent application Ser. No. 13/426,294 filed on Mar. 21, 2012, and continuation-in-part of parent application Ser. No. 12/511,796 filed on Jul. 29, 2009, which is now U.S. Pat. No. 8,395,007 and Ser. No. 12/550,973 filed on Aug. 31, 2009 which is now U.S. Pat. No. 8,227,651, whereby the entire disclosures of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to improved processes and apparatuses for the selective reaction of terpenes (including mono-, sesqui-, di-terpenes, and others in the terpene family), alpha-olefin oligomers (AOO's), and related mono-unsaturated olefins to their respective dimeric product in high purity using heterogeneous acid catalysis concurrent with full utilization of energy created in the process.

Figure 1:
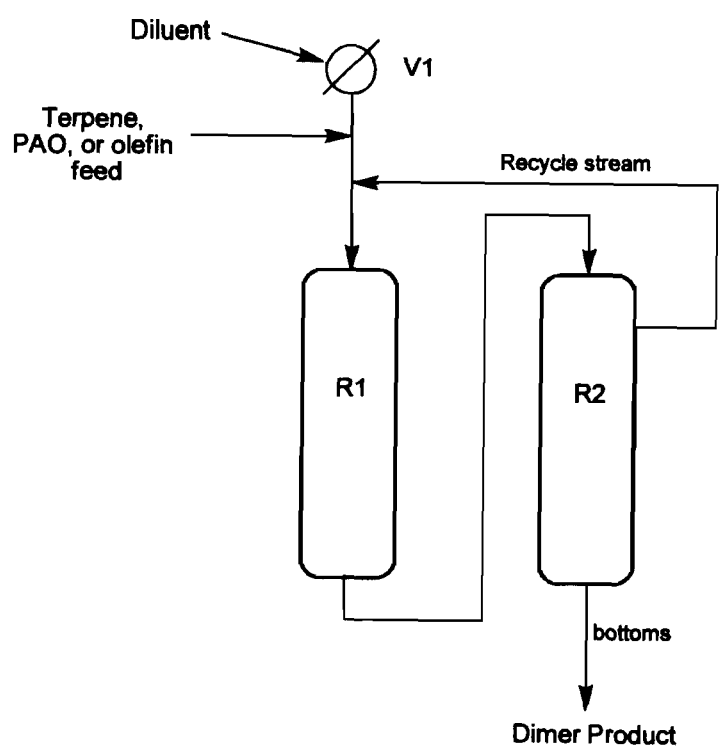
FIG. 1 is a block diagram of a process for the dimerization of terpenes, alpha-olefin oligomers, or related olefins, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to improved processes and apparatuses for the selective reaction of terpenes (including mono-, sesqui-, di-terpenes, and others in the terpene family), alpha-olefin oligomers (AOO's), and related olefins to their respective dimeric product in high purity using heterogeneous acid catalyst concurrent with full utilization of energy created in the process. Embodiments of the invention carry out the efficient dimerization of terpenes, alpha-olefin oligomers (AOO's), and olefins using cost effective catalysts and low cost equipment that are ideally suited for commercialization of jet and diesel biofuel production processes.

An aspect of the invention has a dimerization process including; introducing at least one oligomer-based composition or feedstock selected from the group consisting of terpene(s), alpha-olefin oligomer(s) (AOO), and related olefins, introducing at least one solid acid catalyst to the feedstock for isomerization, recovering and utilizing the initial heat of isomerization, maximizing the concentration of reacting olefin during protonation, utilizing a minimum reaction temperature zone to extend the catalyst lifetime, decreasing trimer and oligomer formations via an active recycle protocol to produce dimerized products in the absence of trimers, tetramers, and up to octamers; and utilizing a first fractionation process that mildly reduces pressure for the evaporation of unreacted feedstock to further produce a purer dimerized product having less than 2 wt-% total of dimers, trimers, and oligomers combined.

Another aspect of the invention has a dimerization system for converting oligomers into dimer products including; at least one oligomer-based composition or feedstock selected from the group consisting of terpene(s), alpha-olefin oligomer(s), and related olefins, at least one solid acid catalyst to the feedstock for isomerization, wherein said oligomer-based composition or feedstock and the catalyst are processed: recovering and utilizing the initial heat of the isomerization, maximizing the concentration of reacting olefin during protonation, utilizing a minimum reaction temperature zone to extend the catalyst lifetime, decreasing trimer and oligomer formations via an active recycle protocol to produce dimerized products in the absence of trimeric, tetrameric, and up to octameric, and utilizing a first fractionation process that mildly reduces pressure for the evaporation of unreacted feedstock to further produce a purer dimerized product having less than 2 wt % total of dimers, trimers, and oligomers combined.

Another aspect of the invention include a dimerized product from oligomers including; at least one oligomer-based composition or feedstock selected from the group consisting of terpene(s), alpha-olefin oilgomer(s)(AOO), and related olefins, at least one solid acid catalyst to the feedstock for isomerization, where the oligomer-based composition or feedstock and the catalyst are converted into a dimerized product having less than 2 wt % total oligomers by processes of isomerization utilizing heat, protonation, maximizing the concentration of reacting olefin during protonation, utilizing a minimum reaction temperature zone to extend the catalyst lifetime, decreasing trimer and oligomer formations via an active recycle protocol to produce dimerized products in the absence of trimeric, tetrameric, and up to octameric, and utilizing a first fractionation process that mildly reduces pressure for the evaporation of unreacted feedstock to produce a dimerized product.

Another aspect of the invention includes a saturated hydrocarbon biofuel including; at least one oligomer-based composition or feedstock selected from the group consisting of terpene(s), alpha-olefin oligomer(s)(AOO), and related olefins; at least one solid acid catalyst to said feedstock for isomerization, wherein said oligomer-based composition or feedstock and said catalyst are converted into a dimerized product having less than 2 wt % total oligomers by processes of isomerization utilizing heat of protonation: maximizing the concentration of reacting olefin during protonation; utilizing a minimum reaction temperature zone to extend the catalyst lifetime; decreasing trimer and oligomer formations via an active recycle protocol to produce dimerized products in the absence of trimeric, tetrameric, and up to octameric; utilizing a first fractionation process that mildly reduces pressure for the evaporation of unreacted feedstock to produce a dimerized product; a hydrogenation system/device to produce fully saturated hydrocarbon dimer products from the either dimerized product; at least one catalyst into the hydrogenation process; a hydrocracking reactor system/device to reduce the molecular weight of the saturated hydrocarbon dimer products and/or to produce a lower boiling fuel product from the fully saturated hydrocarbon dimer products; at least one catalyst into the hydrocracking process; at least one reagent which is introduced into the hydrogenation process and the hydrocracking process; and a second fractionation process to product a fully saturated hydrocarbon biofuel with sufficient flashpoint and cold flow properties from the lower boiling fuel product.

Embodiments of the invention further include initially diluting of the feedstock/oligomer. Embodiments of the invention include at least one terpene selected from the group consisting of monoterpenes, sesquiterpenes, diterpenes, terpenes being linear or having more than one ring, terpenes having at least one site being unsaturated, terpenes having at least one double bond that can be hydrogenated, and terpenes having from about $C_5$ to about $C_{30}$ carbons. Other embodiments include at least one terpene being acyclic having farnesene and/or cyclic having limonene. Embodiments of the invention include at least one AOO having about $C_6$ to about $C_{28}$ carbons. Other embodiments include at least one AOO having bio-2-ethyl-1-hexene.

Embodiments of the invention include active recycle protocol being performed by diluting the feedstock with the recycled and isomerized olefins. Embodiments of the invention include a first fraction process having at least one evaporator selected from the group consisting of at least one wiped film evaporator, thin film evaporator, and other flash type distillation operation. Other embodiments of the invention include a first fraction process having more than one column. Yet other embodiments of the invention include a first fraction process is recycled into the protonation/dimerization process for complete conversion to dimer products. Still yet other embodiments include prior to the first fractionation process a monitoring system is optionally utilized to detect for presence of oligomers.

Embodiments of the invention include reducing pressure during the first fractionation process to such a level that the boiling temperature of isomerized yet non-dimerized feedstock matches the target temperature of the protonation/dimerization process. Embodiments of the invention further include processing either dimerized product through hydrogenation to produce fully saturated hydrocarbon dimer products that can be directly placed in use as diesel and jet/turbine fuels with a flashpoint greater than 61. Embodiments of the invention include the hydrogenation process being selected from the group consisting of at least one trickle bed reactor and/or fixed volume reaction vessel with mechanical stirring. Embodiments of the invention further including introducing at least one catalyst into the hydrogenation process.

Embodiments of the invention include at least one catalyst being transition metals selected from the group palladium, platinum, nickel, and any combination thereof. Embodiments of the invention further include processing the fully saturated hydrocarbon dimer products through a hydrocracking reactor process to reduce the molecular weight of the saturated hydrocarbon dimer products and/or to produce a lower boiling fuel product. Embodiments of the invention further include introducing at least one catalyst into the hydrocracking process. Embodiments of the invention include at least one catalyst selected from the group consisting of palladium, platinum, and nickel or combination thereof being supported on a high surface substrates selected from the group consisting of silicate, aluminate, zeolite, or other mesoporous inorganic support. Other embodiments of the invention include hydrogenation process and the hydrocracking process includes at least one reagent. In embodiments, the process having a reagent includes $H_2$. Embodiments of the invention further including processing the lower boiling fuel product through a second fractionation process to product a fully saturated hydrocarbon biofuel with sufficient flashpoint and cold flow properties.

Other aspects of the invention include a dimer product having less than 1 wt-% but no more than 2 wt-% combined total mass of trimer, tetramer, and oligomers produced by the process. Another embodiment of the invention includes a fully saturated hydrocarbon gas, diesel, jet/turbine biofuel produced by the process. Another aspect of the invention includes a dimerization system for converting oligomers into dimer products including; at least one oligomer-based composition or feedstock selected from the group consisting of terpene(s), poly-alpha-olefin(s), and related olefins, at least one solid acid catalyst to the feedstock for isomerization, where the oligomer-based composition or feedstock and the catalyst are processed by the steps of: recovering and utilizing the initial heat of the isomerization, maximizing the concentration of reacting olefin during protonation, utilizing a minimum reaction temperature zone to extend the catalyst lifetime, decreasing trimer and oligomer formations via an active recycle protocol to produce dimerized products in the absence of trimeric, tetrameric, and up to octameric; and utilizing a first fractionation process that mildly reduces pressure for the evaporation of unreacted feedstock to further produce a purer dimerized product having less than 2 wt % total of dimers, trimers, and oligomers combined.

The dimerization of simple olefins like isobutylene (2-methylpropene) has played a major role in the production petroleum based fuels. These fuels are often referred to as "polymer gasoline." Methods to both simplify and make the process more efficient have been the topic of many patents over the past three plus decades. Methods are continually sought that provide higher selectivity of the targeted product(s) and utilize a minimum of steps and hardware. With the advent and interest in dimerizing larger olefins and bioalkenes, for example terpenes and bio(alpha-olefin oligomers), several new important and pivotal considerations come forth.

Modern oligomerization/dimerization strategies have utilized solid phase catalyst such as Amberlyst-15, solid phosphoric acids, and acid modified clays. U.S. Pat. No. 7,803,978 (1984) describes a process using a water soluble oxygenate modifier, such as an alcohol, is used in conjunction with two oligomerization reactors. This process demonstrates the use of amberlyst-15 catalysts in the process and is primarily focused on isobutylene chemistries.

U.S. Pat. No. 5,877,372 (1999) describes the dimerization of isobutylene using Amberlyst-15, tertiary butyl alcohol as an "enhancing modifier," and isooctane as a diluent in the simulated process. This improved process claims a 90% selectivity to dimer for an isobutylene feed.

A process for dimerizing light olefins is described in U.S. Pat. No. 6,660,898 (2003) where unreacted light olefin is recovered by using a reversible chemical reaction. The premise of the invention is again the use of an alcohol, typically tertiary butyl alcohol, as the "selectivity improving oxygenate." Although specifically pronounced in the invention, an oxygenate must be related to the light olefin in structure or otherwise a complicated product mixture would result that incorporated the oxygenates carbon skeleton.

A process and apparatus for oligomerization was recently described in U.S. Pat. No. 7,803,978 B2 (2010) where at least two oligomerization reactors are utilized in the process. The simulated process described in the patent relates to the oligomerization of light olefins to create "gasoline range product" using a series of oligomerization reactors interconnected. This simulated process also utilizes an "oxygenate modifier" in the process to create gasoline like products. Additional work by the UOP group (UOP LLC, Des Plaines, Ill. (US)) was described in U.S. Pat. No. 8,052,945 B2 (2011) with little change in the process and utilizes an alcohol modifier with simulation of only isobutylene as the light olefin.

Of particular relevance to the current invention are related attempts to dimerize terpenes using a solid acid-catalyst. In one (U.S. Pat. Nos. 4,922,047, 5,847,247, and patent application Ser. No. 12/550,973 filed on Aug. 31, 2009) conversion was achieved in the process where the monoterpene β-pinene was reacted. U.S. Pat. No. 4,922,047 focused on producing mixtures of unreacted terpenes and the dimerized product for use as a solvent. The second patent produced significant trimer product with a specific aim of creating lubricants. Other work in the literature has reported that solid acid catalysts, like Amberlyst-15 and K-Montmonorillite lead to isomerization with only poor conversion to the dimer product when reacting the 2-ethylhexene (Harvey and Quintanna *Energy & Fuels* 2010) in the presence of amberlyst-15 and this was followed up through a patent application. In order to achieve reasonable conversions the expensive fluorinated sulfonic acid resin, Nafion, was required.

What is instantly achieved in this invention is a method for efficiently and selectively dimerizing terpenes, AOO's, and related olefins using common solid acid catalysts and in particular sulfonated-polystyrenes or acid clays. Unlike previous work that has focused on isobutylene or 2-butene, the chemical feeds presented in embodiments of this invention are large and more complicated chemical structures and in particular, can undergo isomerization reactions, skeletal rearrangements, and/or oligomerization/polymerization reactions. The feedstocks discussed in embodiments of this invention may be formed directly or indirectly from a biotic process (e.g. fermentation). Hence, conversion and chemistry performed on these feedstocks must be vigilant to reduce green house gas (GHG) emissions during dimerization and ultimately in a life cycle analysis of the finished biofuel. The instant result of embodiments of this invention is a process that can dimerize a wide array of terpenes, AOO's, and related olefins to diesel and turbine fuels with flashpoints over 61 deg C. using an energy and chemically efficient process and apparatus.

To date, only rather expensive solid supported acid catalysts were thought to be able to dimerize AOO's effectively. Embodiments of the invention provide an unique method for carrying out dimerization of AOO's and other terpenes that pose difficulty in dimerization. Currently there is no process or apparatus that takes AOO's and converts them to dimeric products using cost effective reagents. Embodiments of the invention solve an important limitation to current technology in the area and are critical to the success of the jet and diesel biofuel production, in particular, where high (61° C. or greater) flashpoints. It also is critical for advancement of using terpene and related biofeedstocks.

A dimerization process and apparatus is described where a single catalyst column feeds a single and simple fractionation. The feed of new terpene or AOO is blended with recycle from the single-fraction column at such a rate and ratio that a preselected reaction temperature can be maintained while the heat of isomerization (i.e. excess heat generated), is captured and utilized in the fractionation column. Embodiments of the invention create dimerized products in the absence of trimeric and other by-products, significantly maximize production rates of the desired dimers, harness/capture all energy in the process, and enables longer catalyst lifetime due to reduced reaction temperatures. The products from this process are useful as fuels and/or precursors diesel and turbine/jet fuels.

Embodiments of the invention are based upon the concept of: recovering and utilizing the initial heat of isomerization, maximizing the concentration of reacting olefin during protonation/dimerization, utilizing a minimum temperature in the reaction zone to extend catalyst lifetime, and decreasing or eliminating trimer and oligomer formation via an active recycle protocol. By combining these chemical and engineering factors embodiments of this invention bring to light considerable advantage in the art of preparing dimeric chemicals from a feed of terpenes, alpha-olefin oligomers, and related monounsaturated olefins.

PROPHETIC EXAMPLES

The following prophetic examples are for illustration purposes only and not to be used to limit any of the embodiments.

The "isomerization/dimerization zone" includes solid acid catalysts as Amberlyst-15 or Amberlyst-36. The initial start up of the feed can be diluted with finished dimer product (hydrogenated ideally) or previously isomerized feed to adequately control the heat output. The initial heat of isomerization can be significant for certain feeds and not for others. Once isomerized through protonation, the dimerization is a much less exothermic reaction or possibly endothermic in some cases used in embodiments of the invention.

For the purposes of embodiments of the invention, the "fractionation zone" typically designates a flash type distillation operation under mildly reduced pressure. Multiple columns may be used but a single column is used in this example and one of significant surface area to provide an energy efficient evaporation of the unreacted feed olefin. For example, this can be a thin film evaporator or wiped film evaporator with the bottoms feed directly to a storage tank or directly to the next unit (i.e. hydrogenation process). Embodiments of the invention work when dimerizing feedstocks of six to 20 carbons and is particularly useful for molecules having 8 to 15. This is represented by monoterpenes, sesquiterpenes, and AOO's were very large distillation differences exist between the feed and dimerized product. Furthermore, this process is of particular value where consideration of thermal stability for the feed and/or dimer product is considered as often the case for certain biomaterials.

The "hydrogenation zone" is typically operated as a trickle-bed type of reactor at pressures ranging from 50 to 2000 psig and temperature ranging, but not limited from, about 50 to about 150° C. Other ranges of pressure and temperature can be useful in embodiments of the invention when faster processing is required or the feedstock has limited temperature stability. Alternatively, a continuous batch-process can be employed using a fixed volume reactor vessel with mechanical stirring. For each new feed and dimer product the process is optimized to minimize heating and balance heating requirements with the heat output of isomerization and dimerization. This batch-process does expose the dimer to longer heating times although in the absence of acid catalyst; hence, trimer formation is still eliminated in this improved process.

A "hydrocracking zone" can be added to the process to further tailor the process and apparatus to produce a lower boiling fuel product yet retain a high flashpoint and utilize at least 80% of the original carbon. In some cases this is not necessary and in others a minimum of hydrocracking may be necessary to adjust viscosity, flashpoint, and/or cold flow properties in a way common to those experienced in the art of fuel reformation. Common catalysts for this hydrocracking of the dimers would be metal oxides and typical hydrogen pressures would be 100-2000 psig. Heating would vary depending on the degree of cracking required by substrate and target product.

The hydrocarbon feed used in embodiments of the invention can be neat olefin and it is stressed does not include an oxygenate species. In some cases it may be best to initially dilute the feed with previously isomerized hydrocarbon olefin (also can be hydrogenated) or the product of dimerization is suitable. Once in steady state operation, the recycled and isomerized olefin serves to dilute the feed olefin, thus controlling heat out in the isomerization/dimerization zone. The extent of isomerization should be nearly 100% complete in the isomerization/dimerization zone and dimer formation should be about 5% to about 80% and can be controlled by choice of catalyst, time exposed to the catalyst, and temperature maintained for the isomerization/dimerization zone. Conditions and time in contact with the catalyst should be mild and short enough, respectively, as to avoid formation of trimer, tetramer, and oligomeric product. Suitable feeds for this invention include terpenes of about 5 to about 30 carbons, AOO's of about 6 to about 28 carbons, other mono- and di-olefins of about 5 to about 30 carbons.

In some embodiments of this invention in which a $C_8$-hydrocarbon AOO is dimerized, the initial feed may include about 50% of the finished (i.e. hydrogenated) $C_{16}$-dimer product. The feed can consist of an AOO obtained from biomass through a dehydration/oligomerization process starting with bioalcohols, or be obtained directly from a biological process, or from a petroleum feed involving olefin processing. The $C_8$-AOO obtained from biobutanol is one such feedstock, namely bio-2-ethyl-1-hexene. When obtained using a Ziegler-Natta process from bio-1-butene, the AOO product is a single regio-isomer as shown:

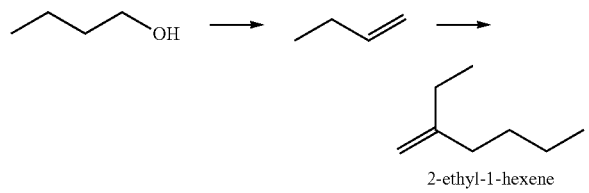

2-ethyl-1-hexene

The 2-ethyl-1-hexene undergoes a rapid acid-catalyzed isomerization reaction that is highly exothermic. Although concurrent dimerization can and will occur to some extent, it is relatively slow compared to isomerization of the AOO that is driven by formation of the more thermodynamically stable internal olefin mixture:

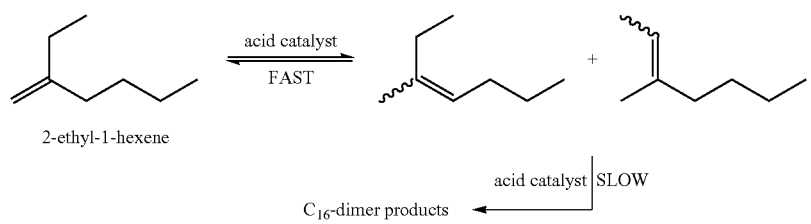

In other embodiments of the invention in which terpene feedstocks are dimerized, the feed compound can be selected from a group of monoterpenes ($C_{10}$), sesquiterpene ($C_{15}$), diterpene ($C_{20}$), or larger hydrocarbon terpenes are possible. The terpene may be linear or include one or more rings in the chemical structure. In embodiments where the terpene has more than one site unsaturation, one or more of the double bonds can be hydrogenated prior to dimerization to produce higher selectivity in the dimerization reaction [Driessen-Holscher in *Adv. Catalysis*, 42, pp 473-505 (1998)]. There are several catalytic systems available for the selective hydrogenation of terpenes including two or more sites of unsaturation. These latter catalysts are effective for both acyclic terpenes including farnesene and cyclic-terpenes such limonene:

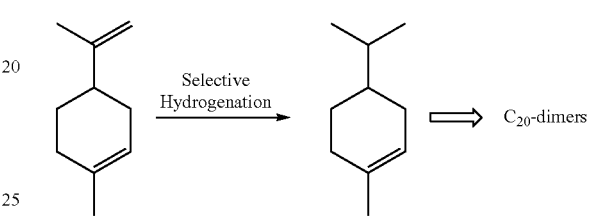

Yet in other embodiments of the invention in which a terpene alcohol is hydrogenated, then dehydrated, and this mono-unsaturated terpene is used as an olefin feed.

Since the terpene is fully isomerized to a thermodynamic mixture of internal olefins, no significant exothermic event will occur upon contact with the acid catalyst and thus no initial dilution of the olefin feed is required in embodiments of the invention:

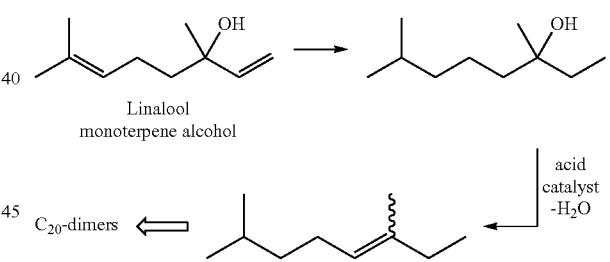

Embodiments of the invention specifically aim to provide a continuous flow system capable of dimerizing terpenes, AOO's, and other olefins to their respective dimers in 100% conversion with better than 98% selectivity for the dimer product. Furthermore, embodiments teach how to utilize inexpensive solid acid-catalysts systems and a means to provide exceptional long catalyst life by optimizing reaction conditions. The dimer products created in embodiments of the invention can be further processed to afford diesel and/or turbine/jet petro- and bio-fuels with flashpoints greater than 61° C.

FIG. 1 shows, in the form of a block diagram, the process flow scheme for converting terpenes, AOO, or olefins to dimeric products. Depending on the feed to the isomerization/dimerization reactor (R1), valve 1 (V1) from the diluent will be used as needed to control the heat generated in the catalyst bed. Typically, the catalyst bed will be included in a jacketed tube-reactor that can pull off the heat and transfer the heat to the fractionator and/or spread the heat uniformly over the entire length of R1. The liquid exiting R1 is monitored to detect formation of oligomers (trimer . . . ) and look to reach a maximum conversion to dimer. When trimer is detected, faster flow rates are applied and/or the temperature is reduced. The process is tuned/optimized for each feed used in the apparatus shown in FIG. 1. Conversion rates to dimer may be between 5 and 80% in a single pass depending on the type of feed and chemical structure. The mixture exiting R1 is all directed to R2 which is a high-surface area fractionation device (e.g. a wiped film evaporator) operating under reduced pressure. Ideally, the pressure is reduced to such a level that the boiling temperature of isomerized yet unreacted feed (under reduced pressure), matches the reaction temperature used in R1, thus minimizing heating/cooling requirements in the process. The bottoms from R2 are the dimer and stated above, reaction temperature and reaction times should be optimized to afford a product with less than 2 wt % or 5 wt % oligomers (e.g. trimer and tetramer). The recycling process is continued until all the feed it converted to dimeric product with no more than 5 wt-% trimer and high products and more typical of this invention is less than 1 wt-%.

Figure 2:
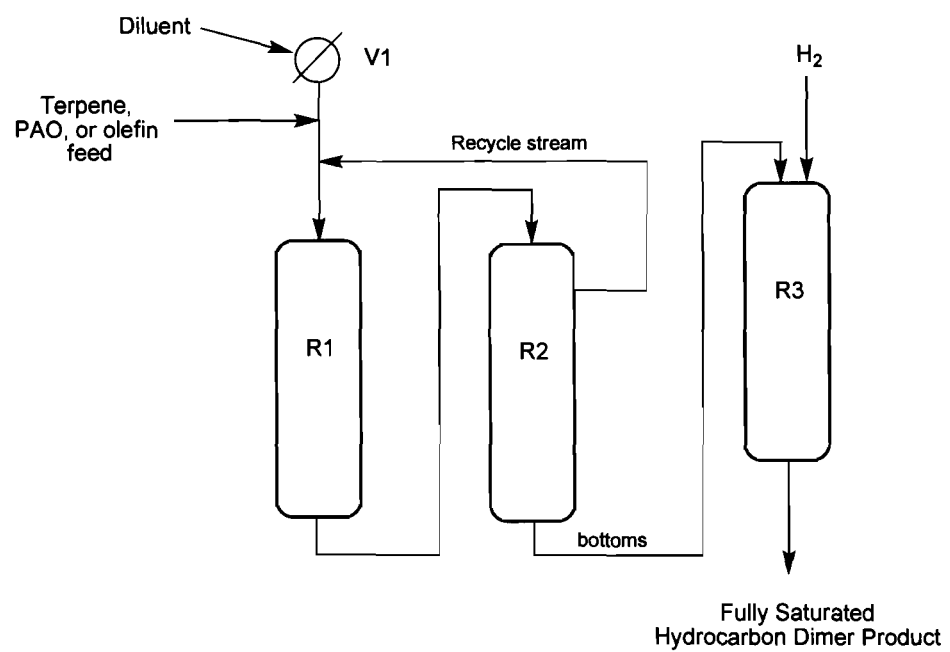
FIG. 2 is a block diagram of a process for the dimerization of terpenes, alpha-olefin oligomers, or related olefins that includes hydrogenation of the dimer product for use in diesel and turbine fuels, according to embodiments of the invention.

The dimers produced in embodiments of the invention are converted to diesel and turbine fuels with a flash point greater than 61° C. by addition of a third reactor that is capable of carrying out hydrogenation so the dimer products become fully saturated hydrocarbons. FIG. 2 shows the addition of R3 which can be trickle bed reactor or a fixed volume reaction vessel provided with mechanical stirring. Typical catalysts for the hydrogenations would include, but not limited to, palladium, platinum, or nickel supported on various solid supports including amorphous carbon and in particular for nickel, aluminum (e.g. Raney-Nickel®). Typical sources of hydrogen can be from the thermal cracking of biomass including, but not limited to, lignin or through hydrogen-producing bacteria that is pressurized to meet the reaction requirements, typically in the range of about 50 to about 2000 psig.

Figure 3:
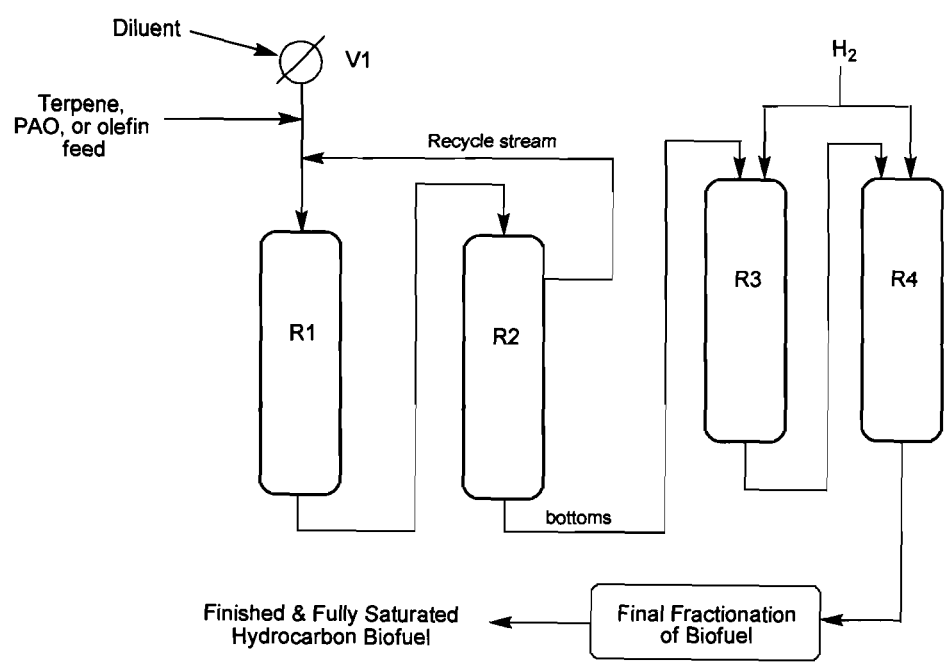
FIG. 3 is a block diagram of a process for the dimerization of terpenes, alpha-olefin oligomers, or related olefins that includes hydrogenation of the dimer product, and then hydrocracking/reforming of the hydrogenated dimer to products useful as gas, diesel and turbine fuels, according to embodiments of the invention.

Addition of a hydrocracking reactor to the process and apparatus provides a method for reducing the molecular weight of the dimeric products while providing a broader distribution of molecular weights which can be considered beneficial for diesel or turbine fuels although not a requirement. As the dimers formed in embodiments of the invention are significantly branched, mild hydrocracking can be used or as those practiced in the art would refer to it as light cracking or light reforming processes. FIG. 3 shows the addition of the hydrocracking reactor (R4) and depending on the desired biofuel characteristics, some fractionation may be required to provide sufficient flash point and cold flow properties.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A dimerization system for converting oligomers into dimer products, comprising:
    at least one oligomer-based composition or feedstock selected from the group consisting of terpene(s), alpha-olefin oligomer(s), and other mono- and di-olefins having from about 5 to about 30 carbon atoms;
    at least one solid acid catalyst for isomerization and dimerization of said at least one oligomer based composition feedstock housed in a minimum temperature zone to extend a lifetime of said at least one solid acid catalyst, and wherein a concentration of said at least one oligomer-based composition or feedstock is maximized during isomerization through protonation;
    a transfer device for recovering and utilizing the initial heat of said isomerization;
    at least one distillation/evaporation device that utilizes said heat of isomerization to actively recycle unreacted or isomerized said at least one oligomer-based composition or feedstock into said minimum temperature zone to produce dimer products with decreased trimers and heavier oligomers formation, and wherein said at least one distillation/evaporation device includes a first fractionation device that reduces pressure for the evaporation of unreacted said at least one oligomer-based composition or feedstock to further produce purer dimer products having less than 2 wt % total of trimers and heavier oligomers, combined;
    a hydrogenation system/device receiving said purer dimer products to produce fully saturated hydrocarbon dimer products that can be directly placed in use as diesel and jet/turbine fuels with a flashpoint greater than 61 ° C.; and
    a hydrocracking reactor system/device to reduce the molecular weight of said fully saturated hydrocarbon dimer products and/or to produce a lower boiling fuel product from said fully saturated hydrocarbon dimer products, said hydrocracking reactor system/device further comprising at least one hydrocracking catalyst selected from the group consisting of palladium, platinum, nickel, and combinations thereof being supported on a high surface substrate selected from the group consisting of silicate, aluminate, zeolite, and other mesoporous inorganic supports.

2. The system according to claim 1, further comprising diluents to initially dilute said at least one oligomer-based composition or feedstock.

3. The system according to claim 1, wherein said terpene(s) is selected from the group consisting of monoterpenes, sesquiterpenes, diterpenes, terpenes being linear or having more than one ring, terpenes having at least one side being unsaturated, terpenes having at least one double bond that can be hydrogenated, and terpenes having from about $C_5$ to about $C_{30}$ carbons.

4. The system according to claim 1, wherein said terpene(s) is acyclic including farnesene and/or cyclic including limonene.

5. The system according to claim 1, wherein said alpha-olefin oligomer(s) have about $C_6$ to about $C_{28}$ carbon atoms.

6. The system according to claim 1, wherein said alpha-olefin oligomer(s), comprises bio-2-ethyl-1-hexene.

7. The system according to claim 1, wherein the actively recycled unreacted or isomerized said at least one oligomer-based composition or feedstock dilutes said at least one oligomer-based composition or feedstock.

8. The system according to claim 1, wherein said first fractionation device comprises at least one evaporator selected from the group consisting of at least one wiped film evaporator, thin film evaporator, and other flash distillation systems.

9. The system according to claim 1, wherein said first fractionation device includes more than one column.

10. The system according to claim 1, wherein said unreacted said at least one oligomer-based composition or feedstock obtained from said first fractionation device is recycled for complete conversion to dimer products.

11. The system according to claim 1, wherein a monitor system/device is utilized prior to said first fractionation device to detect for presence of oligomers.

12. The system according to claim 1, wherein said first fractionation device reduces pressure to such a level that the boiling temperature of isomerized yet non-dimerized said at least one oligomer based composition or feedstock matches the target temperature of said dimerizing of said at least one oligomer-based composition or feedstock.

13. The system according to claim 1, wherein said hydrogenation system/device is selected from the group consisting of at least one trickle bed reactor and fixed volume reaction vessel with mechanical stirring.

14. The system according to claim 1, wherein said hydrogenation system/device comprises at least one hydrogenation catalyst.

15. The system according to claim 14, wherein said at least one hydrogenation catalyst comprises transition metals selected from the group consisting of palladium, platinum, nickel, and any combination thereof.

16. The system according to claim 1, further comprising at least one reagent which is introduced into said hydrogenation system/device and said hydrocracking system/device.

17. The system according to claim 16, wherein said at least one reagent includes $H_2$.

18. The system according to claim 1, further comprising a second fractionation device to produce a fully saturated hydrocarbon biofuel with sufficient flashpoint and cold flow properties from said lower boiling fuel product.

* * * * *